(12) United States Patent
Griego

(10) Patent No.: US 8,647,362 B2
(45) Date of Patent: Feb. 11, 2014

(54) DEVICE WITH DEFLECTABLE DISTAL END AND RELATED METHODS OF USE

(75) Inventor: John A. Griego, Blackstone, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2823 days.

(21) Appl. No.: 10/682,197

(22) Filed: Oct. 10, 2003

(65) Prior Publication Data

US 2005/0080451 A1 Apr. 14, 2005

(51) Int. Cl.
*A61B 17/28* (2006.01)

(52) U.S. Cl.
USPC ........... 606/205; 606/169; 606/170; 606/207; 606/208

(58) Field of Classification Search
USPC ............. 606/1, 167, 169, 170, 205, 206, 207, 606/208; 227/176.1
See application file for complete search history.

(56) References Cited

U.S. PATENT DOCUMENTS 5,690,269 A * 11/1997 Bolanos et al. ............ 227/176.1
5,700,275 A 12/1997 Bell et al.
6,063,098 A * 5/2000 Houser et al. ................ 606/169
6,343,731 B1 2/2002 Adams et al.
6,398,795 B1 6/2002 McAlister et al.
6,478,210 B2 11/2002 Adams et al.
6,520,971 B1 2/2003 Perry et al.
6,544,271 B1 4/2003 Adams et al.
2002/0120253 A1 8/2002 Ouchi

FOREIGN PATENT DOCUMENTS

WO    WO 97/12557 A    4/1997
WO    WO 99/52489 A    10/1999
WO    WO 02/07611 A    1/2002

OTHER PUBLICATIONS

International Search Report and Written Opinion in PCT/US2004/030913 mailed Feb. 9, 2005.

* cited by examiner

*Primary Examiner* — Vy Q Bui
(74) *Attorney, Agent, or Firm* — Fay Kaplun & Marcin, LLP

(57) ABSTRACT

A deflecting method and deflecting apparatus allows the distal end of device, for example an endoscopic medical device, to be remotely and adjustably deflected from a straight configuration to a deflected configuration. Manipulating a proximal handle causes the deflection, controls actuation of an end effector assembly on the distal end, and straightens the deflecting apparatus back to its original configuration.

22 Claims, 7 Drawing Sheets

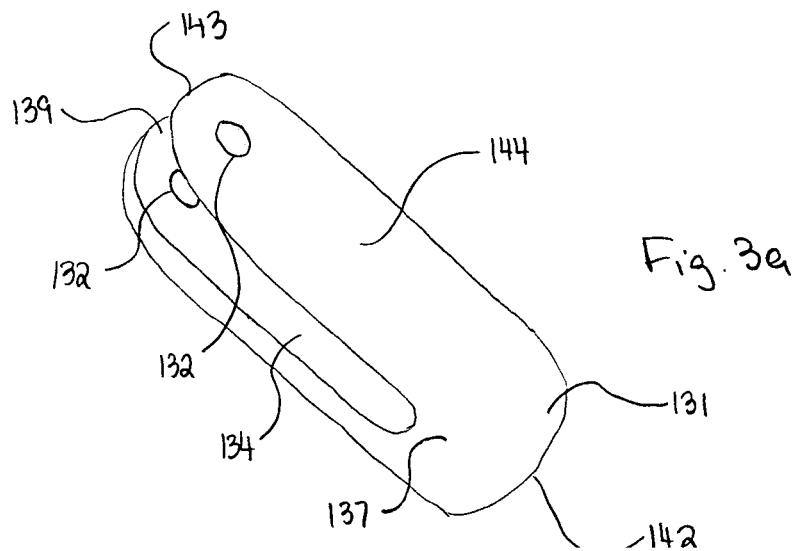
Fig. 3a
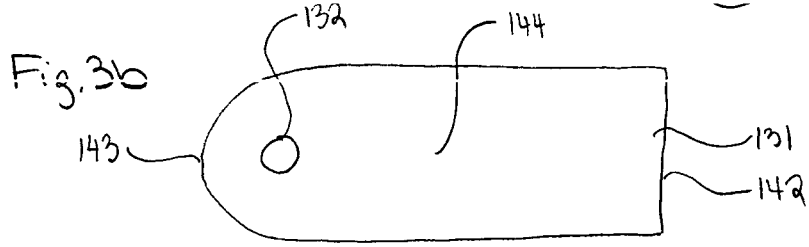
Fig. 3b
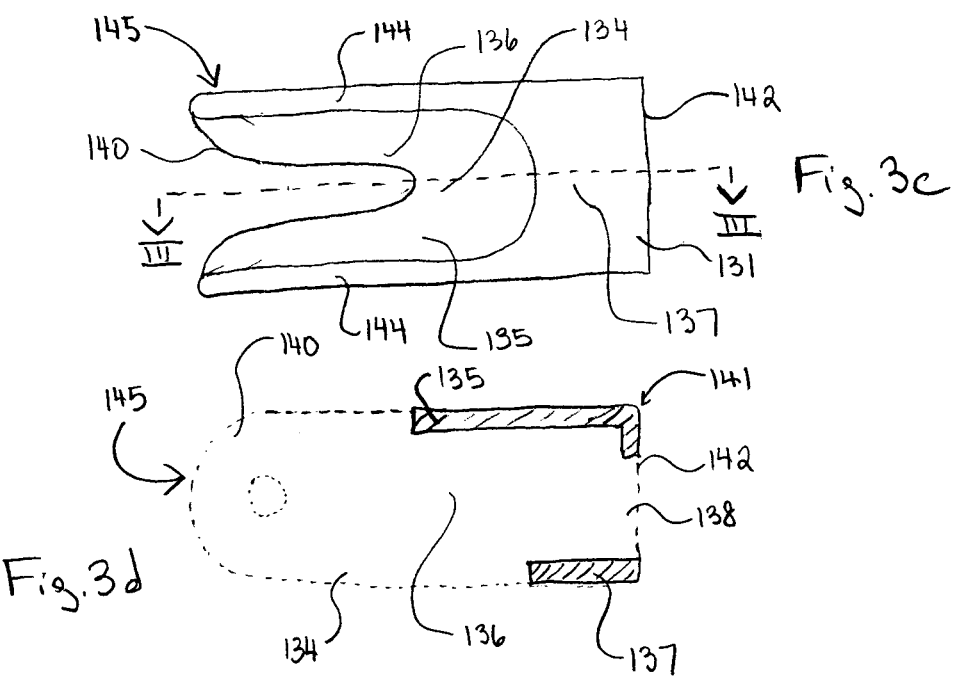
Fig. 3c
Fig. 3d

DEVICE WITH DEFLECTABLE DISTAL END AND RELATED METHODS OF USE

DESCRIPTION OF THE INVENTION

Field of the Invention

The invention relates to a device having a deflectable distal end and methods of using such a device. More specifically, the invention relates to a device having a distal end that remotely and adjustably deflects from a straight configuration to a configuration that is at least up to 90 degrees from the straight configuration. The device may be, for example, a medical device, such as an endoscopic medical device.

Background of the Invention

Lesions or other undesirable tissue may form in internal organs or other tissue tracts within the body. Such undesirable tissue may simply irritate the surrounding tissue or, in a more serious case, may be cancerous and if not quickly removed cause deterioration of the surrounding tissue and subsequent failure of the organ or tissue tract.

One method of removing the undesirable tissue is through a conventional open surgical procedure during which the undesirable tissue is cut away. Such an open surgical procedure, however, is highly invasive, expensive, relatively traumatic to the patient, and would be inappropriate for many situations where only a small amount of tissue, for example, a small lesion, needs to be removed.

A procedure that may used to remove the undesirable tissue when an open surgical procedure is impractical is full thickness resection. In that procedure, a full thickness resection device (FTRD) is advanced endoluminally to the desired portion of the body, for example through a working channel of an endoscope, and positioned near the undesirable tissue. A grasping device, such as an endoscopic grasper having a pair of jaws at a distal end, grabs the undesirable tissue and brings the undesirable tissue into an open distal portion of the FTRD. The FTRD then resects the undesirable tissue and connects the surrounding tissue together to close the hole created by the resection. The FTRD containing the undesirable tissue then is advanced out of the body. An example of an FTRD and related method of use is disclosed in U.S. Pat. No. 6,398,795 to McAlister et al., the full disclosure of which is hereby incorporated by reference.

A problem with current FTRDs, however, is in the positioning of the grasping device, and particularly the grasper jaws located at the distal end of the device. The jaws need to be maneuvered to the tissue to be resected. While the positioning of the grasper jaws may be assisted by the presence of a preformed bend in an elongate, tubular member leading up to the grasper jaws, it still may be difficult to position the grasper jaws so that they grasp the tissue to be resected. This difficulty in positioning may result in procedures that are more complex and longer than necessary, and may cause undesired removal of surrounding healthy tissue.

It is accordingly an object of the invention to have a device with a deflectable distal end, for example a grasping device with a deflectable distal end so that grasper jaws can be remotely and adjustably deflected from a longitudinal axis of the device, for easier, faster, and more precise positioning of the grasper jaws.

SUMMARY OF THE INVENTION

In accordance with the invention, an embodiment of the invention includes an end effector apparatus having a deflecting mechanism having a proximal portion, a distal portion, and a redirection mechanism between the proximal portion and the distal portion, the redirection mechanism configured to allow the distal portion to be redirected relative to the proximal portion. The end effector apparatus also has an end effector assembly coupled to the distal portion and a first actuator coupled to the deflecting mechanism to redirect the distal portion with respect to the proximal portion via the redirection mechanism.

In accordance with another aspect of the invention, an embodiment of the invention includes an endoscopic medical device having an end effector assembly, a deflecting mechanism coupled to the end effector assembly, the deflecting mechanism including a proximal portion, a distal portion, and a pivot portion connecting the proximal portion to the distal portion, the pivot portion configured to allow the distal portion to deflect relative to the proximal portion, and a handle. The endoscopic medical device also has an elongate member connecting the handle to the deflecting mechanism, an actuator wire extending through the elongate member and connecting the handle to the end effector assembly, and a deflector wire extending through the elongate member and connecting the handle to the deflecting mechanism. The handle of the endoscopic medical device is configured to control the end effector assembly via the actuator wire and the deflecting mechanism via the deflector wire.

In accordance with yet another aspect of the invention, an embodiment of the invention includes a method of performing a procedure with an end effector apparatus by providing a distal end effector assembly coupled to an elongate member in a substantially straight configuration, redirecting the distal end effector assembly such that the distal end effector assembly and the elongate member are no longer in a substantially straight configuration, and actuating the distal end effector assembly to perform the procedure.

In accordance with yet another aspect of the invention, an embodiment of the invention includes an endoscopic medical procedure that is performed by providing an endoscopic medical device having an elongate member with a redirecting mechanism and an end effector assembly at a distal end of the elongate member, with the redirecting mechanism in a substantially straight configuration, advancing the elongate member into a body lumen until the distal end is proximate a treatment site, and redirecting the redirecting mechanism such that the redirecting mechanism is no longer in the substantially straight configuration to position the end effector assembly toward the treatment site. The endoscopic medical procedure is also performed by actuating the end effector assembly to perform a medical procedure and returning the redirecting mechanism to the substantially straight configuration.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

FIG. 1b is a side view of the deflecting mechanism of FIG. 1a.

FIG. 1c is a side view of an end effector assembly connected to the deflecting mechanism of FIG. 1a.

FIG. 2a is a perspective view of a proximal portion of the deflecting mechanism of FIG. 1a.

FIG. 2b is a side view of the proximal portion of FIG. 2a.

FIG. 2c is a top view of the proximal portion of FIG. 2a.

FIG. 3a is a perspective view of a distal portion of the deflecting mechanism of FIG. 1a.

FIG. 3b is a side view of the distal portion of FIG. 3a.

FIG. 3c is a top view of the distal portion of FIG. 3a.

FIG. 3d is a cross-sectional view along line III-III of FIG. 3c.

FIG. 4 is a schematic view of a pivot portion of the deflecting mechanism of FIG. 1a.

DESCRIPTION OF THE EMBODIMENTS

Reference will now be made in detail to the present exemplary embodiments of the invention illustrated in the accompanying drawings. Wherever possible, the same reference numbers will be used throughout the drawings to refer to the same or like parts.

In the various embodiments, the invention pertains to a mechanism for deflecting a distal end of a device. The device may include a proximal handle, a distal end effector assembly (such as grasper jaws), and an elongate member connecting the handle to the end effector assembly. A deflecting mechanism may be included along the elongate member, for example at the end of the elongate member proximate the end effector assembly. In the embodiments, a user may manipulate a portion of a handle that controls the deflecting mechanism. The manipulation may cause the deflecting mechanism, which was in a straight configuration, to bend. Depending on the amount of manipulation, the bending of the deflecting mechanism causes the distal portion of the device to assume an up to at least 90 degrees angle relative to an axis of the elongate member. Once a desired bend and angle is attained, the user may position the end effector assembly proximate to a desired position to perform an operation. The user then may manipulate another portion of the handle, causing the end effector assembly on the distal end of the device to actuate, the amount of actuation dependent on the amount of manipulation of the handle. Actuation of the end effector assembly performs the desired operation, such as grasping of tissue. If desired, at this point in the procedure or later, so that the device may be removed from a body in the case of a medical device, the user may once again manipulate the portion of the handle that controls the deflecting mechanism, causing the deflecting mechanism to straighten back to substantially its original configuration.

Figure 5:
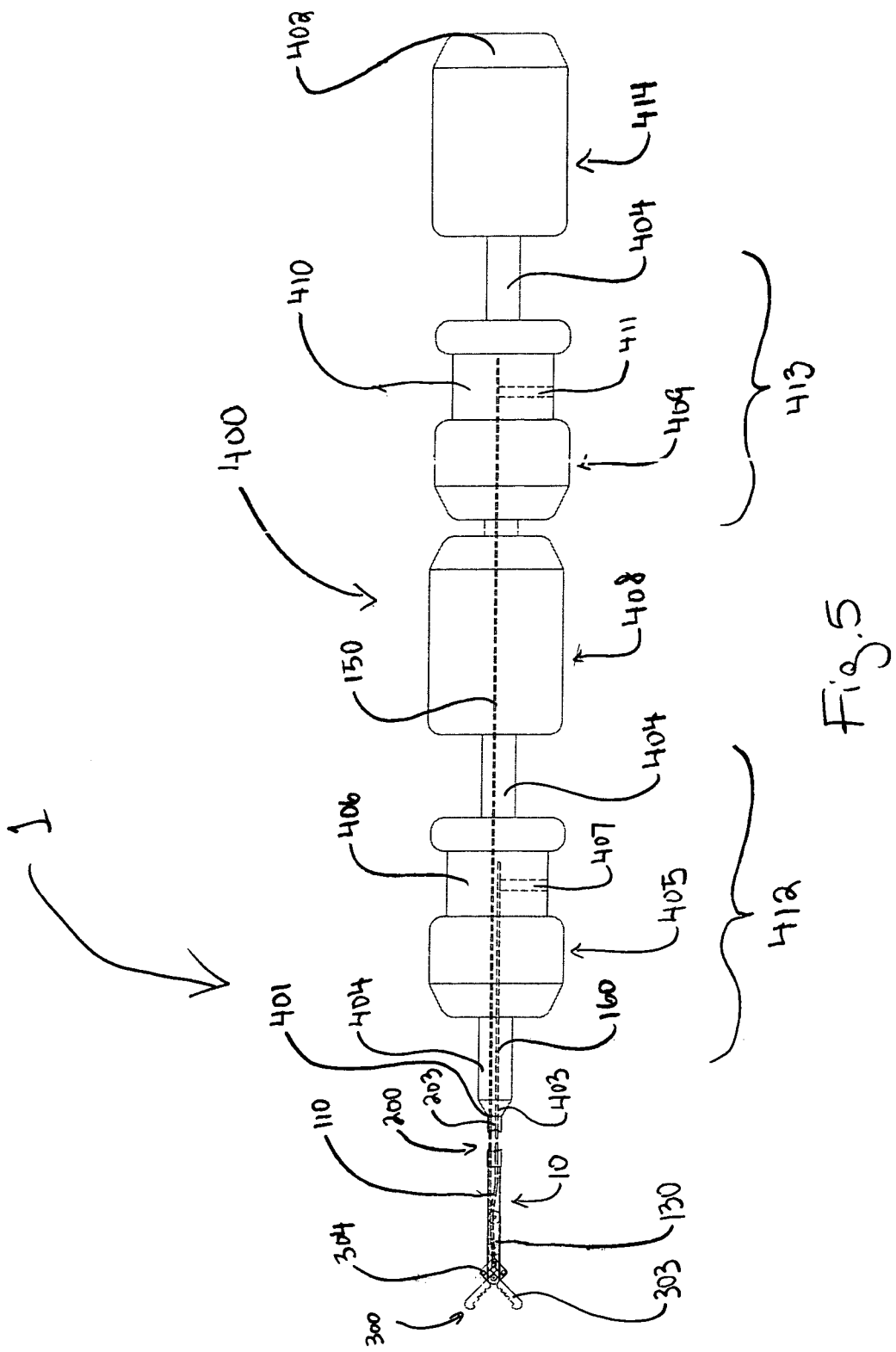
FIG. 5 is a schematic view of a medical device, showing the proximal handle portion connected to the deflecting mechanism of FIG. 1a, an elongate shaft, and end effectors.

FIG. 5 shows an exemplary embodiment of a device 1 including a deflecting mechanism 10. Device 1 is an endoscopic medical device and, more particularly, an endoscopic grasper. As will be explained below, however, any other type of device that requires deflecting a distal end may include a deflecting mechanism according to this invention.

As its main components, device 1 includes deflecting mechanism 10, an end effector assembly 300, a handle portion 400, an elongate member 200 connecting handle portion 400 to end effector assembly 300, and a deflector wire 150 an actuator wire 160 that actuate deflecting mechanism 10 and end effector assembly 300, respectively.

As shown in the Figures, deflecting mechanism 10 has a proximal end 12 and a distal end 11. The deflecting mechanism includes a proximal portion 110, a distal portion 130, and a pivot portion 170. FIGS. 1a-1b and 2a-2d depict an exemplary embodiment of proximal portion 110. Proximal portion 110 may have a generally circular cross-sectional shape or any other suitable shape permitting connection to other parts of device 1 and advancement through an endoscope working channel, an FTRD, or a tissue tract. Proximal portion 110 includes an interface 111 on its proximal end 121 configured to connect with elongate member 200. The interface 111 may be circular in shape and define a proximal opening 118 leading to a wire shaft 116 inside portion 110. Both proximal opening 118 and wire shaft 116 may receive and allow longitudinal movement of wires, for example, deflector wire 150 and actuator wire 160. Moving toward its distal end 122, proximal portion 110 includes a wire gap wall 117 on one side, a wire containing wall 115 on an opposite side, and sidewall 123 connecting the wire gap wall 117 to the wire containing wall 115.

The wire gap wall 117 may have the shortest length of the walls, leaving a wire gap 114. Wire gap 114 allows movement of wires between the sidewalls 123 during deflection of the deflecting mechanism 10. The edge of wire gap wall 117 proximate wire gap 114 may be configured and/or composed of material to reduce friction and resist pressure exerted on it by at least one wire that may press against it during deflection and/or actuation. The edge of wire gap wall 117 proximate the wire gap 114 may also be configured and/or composed of a material to resist wearing away from the longitudinal movement of the deflector wire 150 and actuator wire 160 along the edge. The wire containing wall 115 is longer than the wire gap wall 117 and shorter than the sidewalls 123. Proximal portion 110 defines a distal portion receiving area 120 at its distal end 122.

In the embodiment shown, sidewalls 123 are the longest portions of proximal portion 110 and may each have near distal end 122 a pivot interface 112 configured to assist the connection of proximal portion 110 to distal portion 130. The portions of sidewalls 123 next to wire gap 114 may be configured and/or composed like the edges of the wire gap walls 117 next to the wire gap 114, as set forth above. Pivot interfaces 112 of sidewalls 123 may be holes that are generally circular in shape and axially aligned with each other. Pivot interfaces 112 receive and retain pivot couplings 171, as will be described below, and allow rotation of pivot couplings 171 within them. Between the pivot interfaces 112 of sidewalls 123 may be distal gap 119 to accept, among other things, a portion of distal portion 130. The distal ends of sidewalls 123, and particularly the external surfaces of sidewalls 123, may be rounded and/or otherwise configured (for example, composed of certain materials) so as to minimize irritation and/or damage to tissue that it may come into contact with.

FIGS. 1a-1b and 3a-3d depict an exemplary embodiment of distal portion 130 of deflecting mechanism 10. The distal portion 130 includes an end effector assembly interface 131 on its distal end 142 configured to connect with end effector assembly 300. The end effector assembly interface 131 generally may be circular in shape and define a distal opening 138 leading to a wire shaft 136. Distal opening 138 and wire shaft 136 receive and allow longitudinal movement of wires, for example, deflector wire 150 and actuator wire 160. Distal opening 138 communicates with a portion of end effector assembly 300.

Distal portion 130 also includes a wire gap wall 137 on one side, a wire containing wall 135 on the opposite side, and sidewalls 144 connecting wire gap wall 137 to wire containing wall 135. Wire gap wall 137 is the shortest of these walls, leaving a wire gap 134 that allows movement of wires between the sidewalls 144 during deflection. The edge of the wire gap wall 137 proximate the wire gap 134 may be configured and/or composed of material to reduce friction and resist pressure exerted on it by at least one wire pressed up against during deflection and/or actuation. The edge of the wire gap wall 137 proximate the wire gap 134 may also be configured and/or composed of material to resist wearing away from the longitudinal movement, for example, of the deflector 150 and actuator wire 160 along the edge. The wire containing wall 135 is longer than the wire gap wall 137 and shorter than the sidewalls 144. Wire containing wall 135 may also have a gap starting from proximal end 143 and narrowing unit it reaches approximately the mid-section of the distal portion 130 and/or sidewalls 144.

In another exemplary embodiment, the sidewalls 144 are the longest portions of the distal portion 130 and may each have near proximal end 143 a pivot interface 132 configured to assist connection of the distal portion 130 to the proximal portion 110. The portions of the sidewalls 144 next to the wire gap 134 may be configured and/or composed like the edges of the wire gap walls 137 next to the wire gap 134 as set forth above. Pivot interfaces 132 of sidewalls 144 may be holes that are generally circular in shape and axially aligned with each other. Pivot interfaces 132 receive and retain pivot couplings 171, as will be describe below, and allow the free rotation of pivot couplings 171 within them. Between the pivot interfaces 132 of sidewalls 144 may be proximal gap 139 to accept, among other things, portions of deflector wire 150 and actuator wire 160. Between the sidewalls 144 may also be wire receiving gap 140, wire gap 134, and/or wire shaft 136. Disposed around proximal end 143 of distal portion 130 may be proximal portion insertion zone 145 configured to be inserted into distal gap 119 between the distal ends 122 of sidewalls 123 of proximal portion 110. The proximal ends of sidewalls 144, for example external surfaces of sidewalls 144 opposite wire shaft 136, may be rounded and or otherwise configured (for example, composed of certain materials) so as to minimize irritation and/or damage to tissue that it may come into contact with.

Near end effector assembly interface 131, distal portion 130 includes a deflector wire connector 141. Connector 141 may be disposed on a portion of the wire gap wall 137 near distal opening 138. Deflector wire 150 may connect to connector 141, for example, by welding or more specifically laser welding. Any other method of connecting deflector wire 150 to connector 141 or any other portion of distal portion 130, for example, using adhesives or any other type of joining material/components, is also acceptable. Other methods of connecting the deflector wire 150 to the connector 141 include a free pivot pin, a ball and socket, or a clevis. Deflector wire 150 may be fixed to connector 141 or movably connected to, for example, allow deflector wire 150 to shift and/or rotate with respect to connector 141 while still maintaining a connection. Deflector wire 150 may be joined to connector 141 such that the deflector wire 150 is not parallel to the longitudinal axis of the distal portion 130. For example, deflector wire 150 may be angled so that it is joined to connector 141 at its distal end, and then proceeds toward the wire gap 134 and/or proximal gap 139 of distal portion 130. This orientation may assist the deflecting of the deflecting mechanism 10, a process which will be described in further detail below.

Figure 1A:
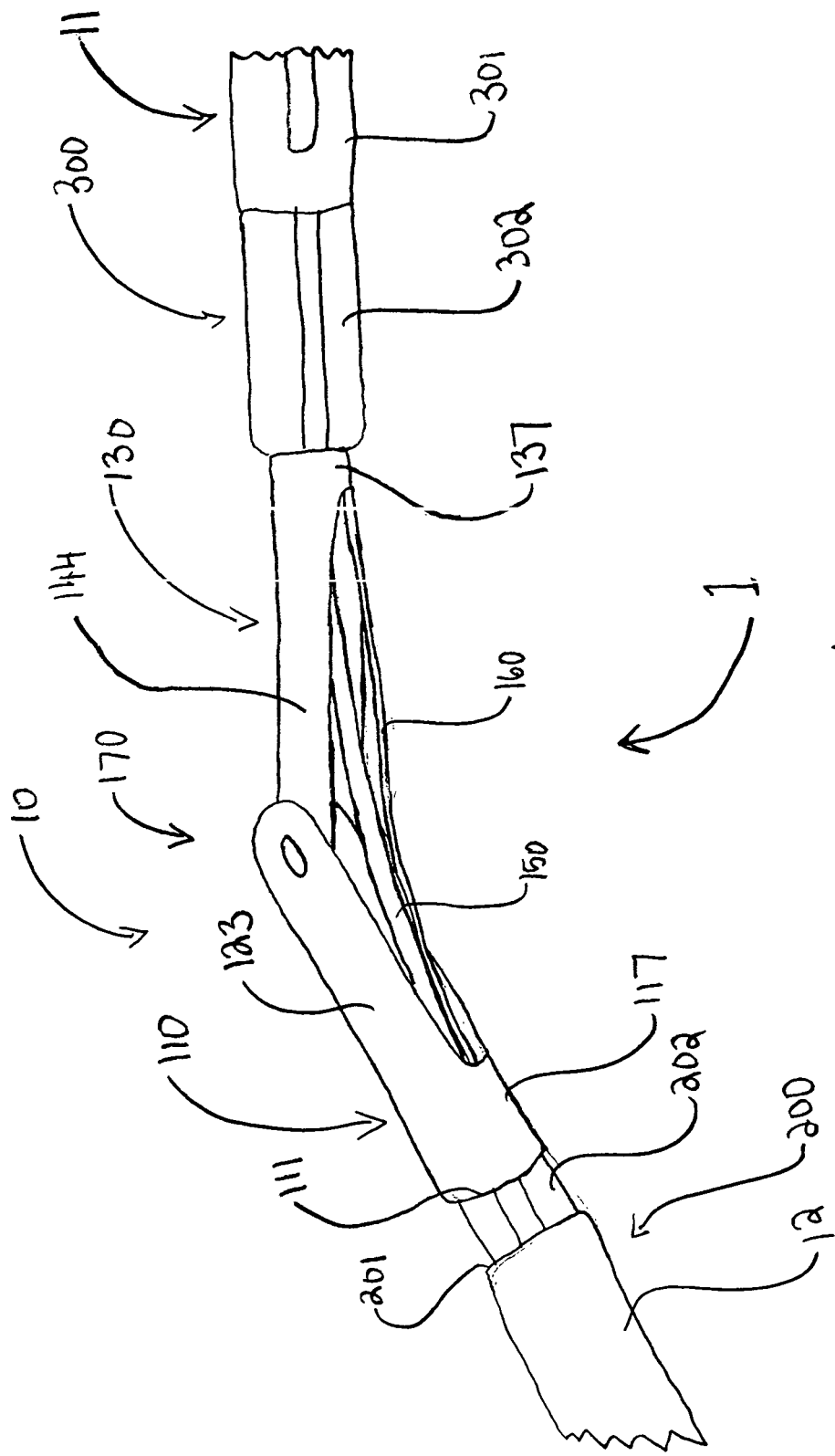
FIG. 1a is perspective view of a deflecting mechanism, according to an embodiment of the present invention.
Figure 1B:
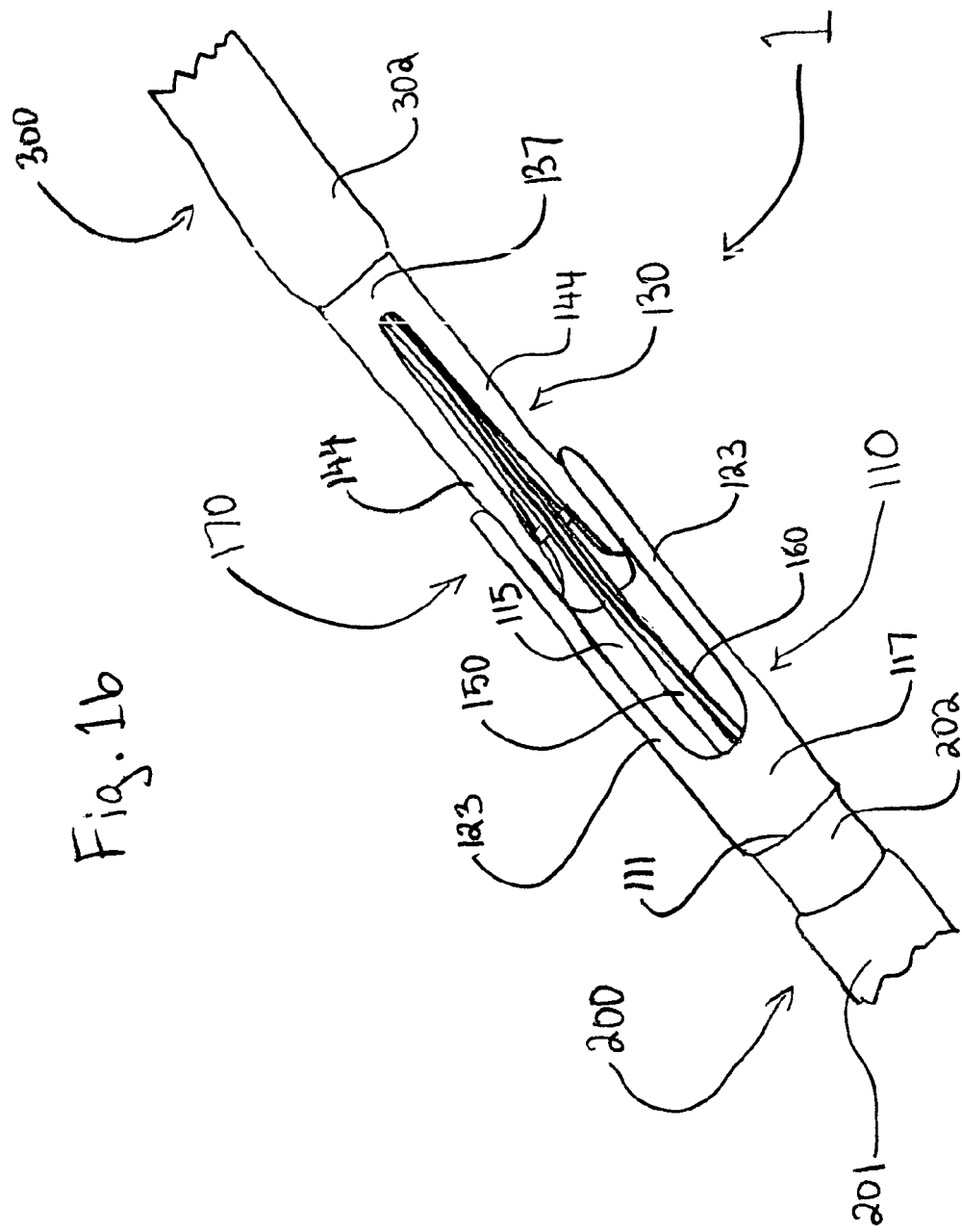
Figure 1C:
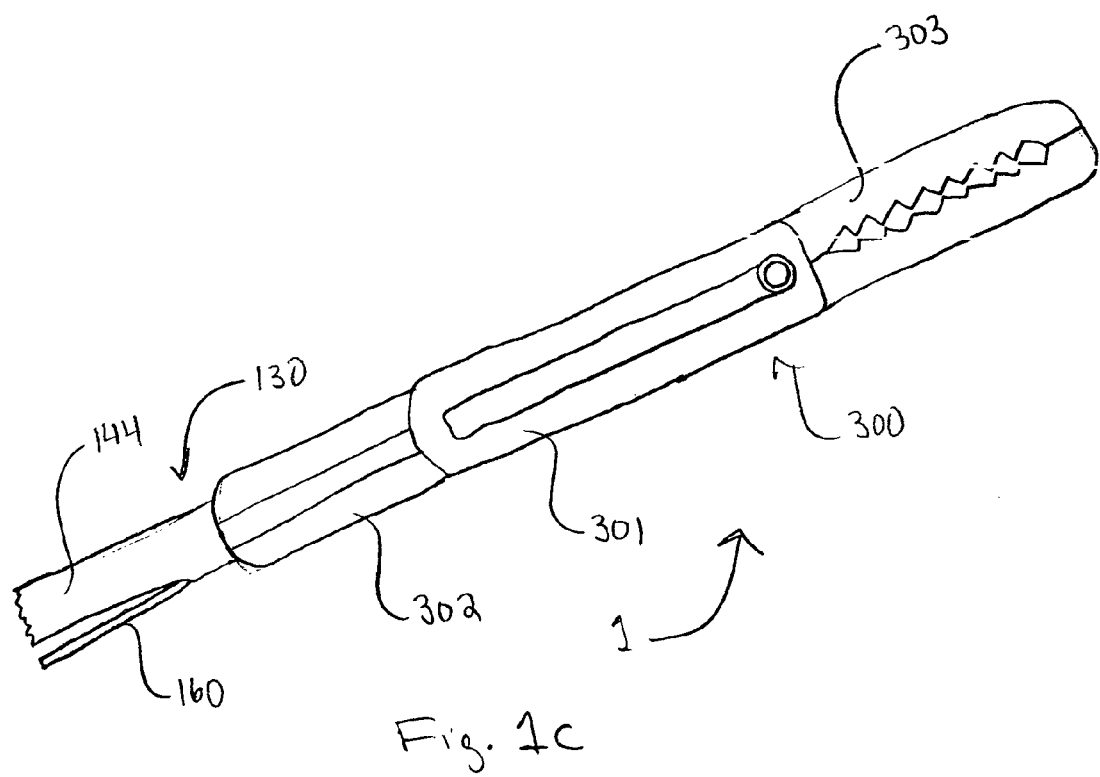
Figure 2A:
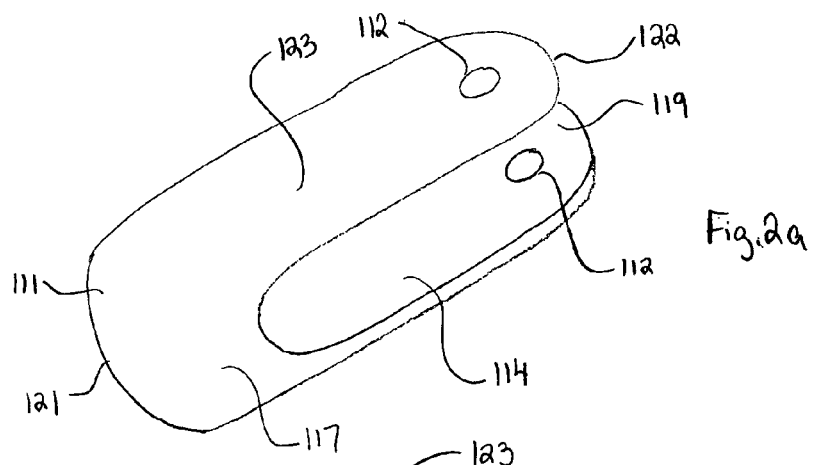
Figure 2B:
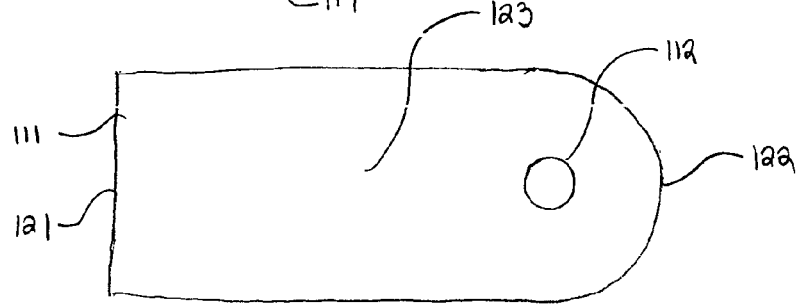
Figure 2C:
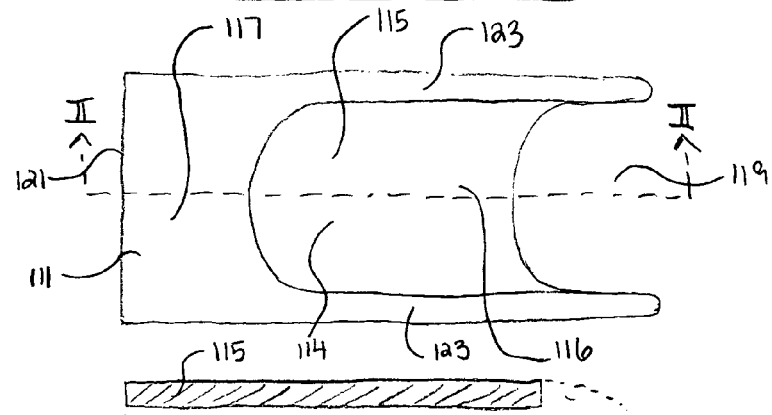
Figure 2D:
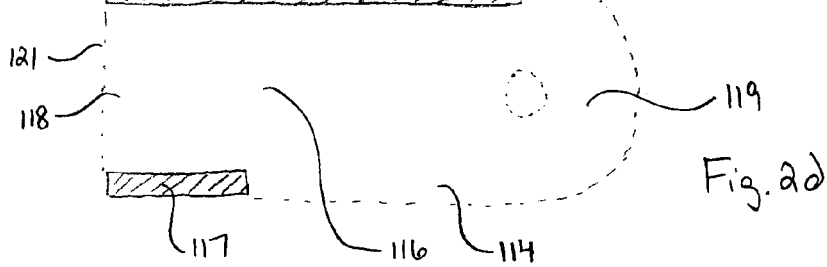
FIG. 2d is a cross-sectional view along line II-II of FIG. 2c.
Figure 4:
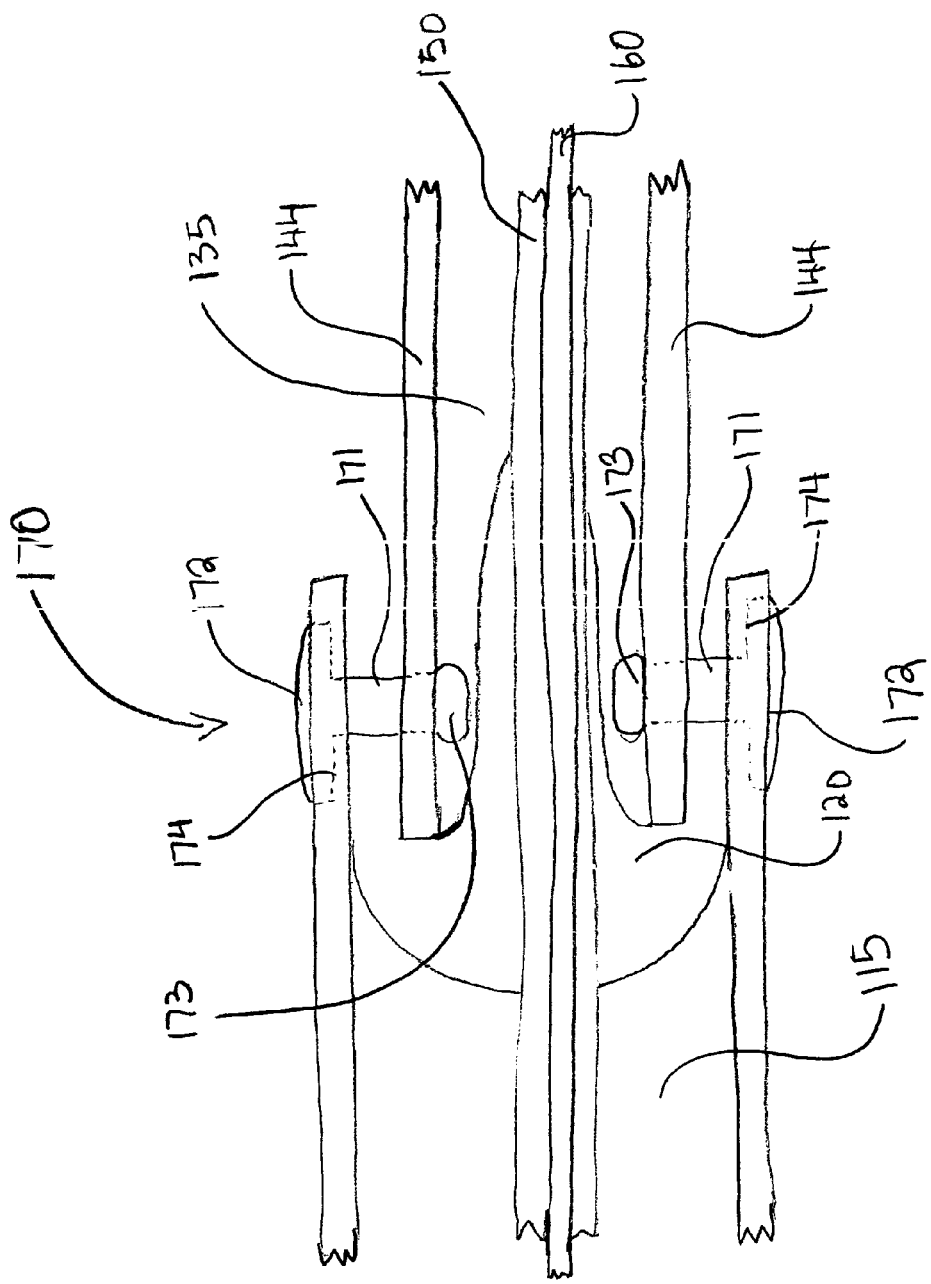

FIGS. 1*a*-1*b* and 4 depict an exemplary embodiment of the pivot portion 170 of deflecting mechanism 10. Pivot portion 170 joins the proximal portion 110 with the distal portion 130. Specifically, the pivot interface 112 of the proximal portion 110 may be connected to the pivot interface 132 of distal portion 130 by pivot couplings 171. The pivot couplings 171 may be comprised of a stainless steel mandel, and more specifically a U-shaped through mandrel to allow room for the wires. Insertion of pivot couplings 171 through pivot interfaces 112 and 132 connects proximal portion 110 and distal portion 130. The pivot interfaces 112, 132 retain the pivot coupling 171. For example, the pivot couplings 171, once inserted through both pivot interfaces 112, 132, may be deformed, for example, at the insertion ends 173 so that the pivot couplings 171 can no longer be removed from the pivot interfaces 112, 132. In another example, the pivot interface 112 of the proximal portion 110 may have a recess 174 configured to accept and retain the recess interface 172 of the pivot coupling 171. An adhesive may be placed in the pivot recess 174 prior to inserting the insertion end 173 of the pivot coupling 171 through the pivot interface 112 of the proximal portion 110, thus allowing the adhesive to join the recess interface 172 with the pivot recess 174 when the recess interface 172 is inserted. The epoxy adhesive, however, may also be placed on the pivot interface 132 of the distal portion. In yet another example, the pivot coupling may be welded, or more specifically laser welded, to either of the distal or proximal portions. The recess interface 172 may be configured so that it is flush with the external portion of the sidewall 123 of the proximal portion 110, for example, to minimize sharp edges and/or protrusions that may irritate and/or damage tissue when it enters and/or is advanced in a tissue tract or internal organ or catch onto a working channel of an endoscope.

The pivot portion 170 permits the proximal portion 110 and distal portion 130 to rotate with respect to each other around an axis formed by the central axes of the pivot couplings 171 and/or the pivot interfaces 112, 132. For example, the pivot couplings 171 may be rotatably fixed with respect to the proximal portion 110, allowing the distal portion 130 to rotate with respect to the pivot couplings 171, or the pivot couplings 171 may be rotatably fixed with respect to the distal portion 130, allowing the proximal portion 110 to rotate with respect to the pivot couplings 171. In another example, both the proximal portion 110 and the distal portion 130 may be rotatable with respect to the pivot couplings 171.

The arrangement of the proximal portion 110, distal portion 130, and pivot portion 170 allows deflecting mechanism 10 to bend in one direction and return to its initial straight configuration. In the embodiment shown, the wire containing walls 115, 135 are on the same side and the wire gaps 114, 134 and wire gap walls 117, 137 are on the other side. Accordingly, the deflecting mechanism 10 may bend such that the external portions of the wire gap walls 117, 137 rotate towards each other, and that the external portions of the wire containing walls 115, 135 rotate away from each other. Once bent in that direction, the arrangement of the proximal portion 110, distal portion 130, and pivot portion 170 would then permit the deflecting mechanism 10 to bend or pivot back such that it returns to its original straight configuration. However, once back in this original straight configuration, or even in its initial straight configuration the arrangement of the proximal portion 110, distal portion 130, and pivot portion 170 may prevent the proximal portion 110 and distal portion 130 from further rotating such that the external portions of the wire gap walls 117, 137 rotate away from each other, and that the external portions of the wire containing walls 115, 135 rotate towards each other. For example, the wire containing walls 115, 135 may be configured such that in a straight configuration, the external portion of the wire containing wall 135 contacts the internal portion of wire containing wall 115, thus preventing bending and/or pivoting of the deflecting mechanism such that the wire containing walls 115, 135 rotate towards each other when in a straight configuration.

The arrangement of the pivot portion 170, proximal portion 110, and distal portion 130 permit bending of the deflecting mechanism 10 such that the central longitudinal axes of the proximal portion 110 and the distal portion 130, as measured extending from the pivot portion 170, go from forming a straight 180 degree angle to forming down to at least a 90 degree angle. The deflecting mechanism 10 may be configured to bend such that the central longitudinal axes of the proximal portion 110 and the distal portion 130 form less than a 90 degree angle, for example, so that a portion of sidewall 144 of the distal portion 130 enters the wire gap 114 of the proximal portion 110 and/or the wire gap walls 117, 137 almost come into contact with each other.

FIGS. 1a-1b and 5 depict an exemplary embodiment of elongate member 200 of the device 1. Elongate member 200 essentially comprises a hollow tube to connect the handle 400 to the deflecting mechanism 10. In the case of an endoscopic device, elongate member 200 would have a length and flexibility to extend from a point outside the body and through a tortuous body lumen proximate to an operation site.

Member 200 has a body 201 which comprises, for example, a stainless steel coil covered with a nylon sheath. The coil allows flexibility as the member 200 winds its way through tortuous anatomy and also prevents crushing, for example of member 200, from occurring when tension is applied to the actuator or deflector wires 150, 160 via the handle 400. However, other material compositions and configurations, for example a metal tube with a rubber or plastic covering, are also comtemplated. Body 201 may have on one end a deflector interface 202 configured to connect, for example, with the connector interface 111 on the proximal end 121 of the proximal portion 110. A central hollow portion of deflector interface 202 communicates on one side with a central hollow portion of body 201, and on the other side with the proximal opening 118 of the connector interface 111. The central hollow portion of the deflector interface 202 and/or the central hollow portion of the body 201 is configured to receive and allow the longitudinal movement of wires, for example, deflector wire 150 and actuator wire 160.

Elongate member 200 may also have on its proximal end a handle interface 203. The handle interface 203 connects to an interface 403 on a distal end 401 of the handle portion 400. The central hollow portion of the handle interface 203 communicates with the central hollow portion of the body 201 and a central hollow portion of a central shaft 404 of the handle 400, to allow the longitudinal movement of wires, for example, deflector wire 150 and actuator wire 160. In another example, the elongate member 200 and proximal portion 110 of the deflecting mechanism 10 may be one continuous piece of material.

FIGS. 1a-1c and 5 depict an exemplary embodiment of end effector assembly 300 of the device 1. The end effector assembly 300 may be any type of medical or non-medical end effector assembly which may require deflecting. The end effector assembly 300 may have an end effector assembly body 301 which comprises, for example, an actuatable grasper 303. The grasper 303 may have opposing jaw portions configured to grasp and/or cut tissue. The end effector assembly body 301 may have on one end a deflector interface 302 configured to connect, for example, with the end effector assembly interface 131 on the distal end 142 of the distal portion 130. A central hollow portion of the deflector interface 302 communicates on one side with a central hollow portion of the end effector assembly body 301, and on the other side with the distal opening 138 of the end effector assembly interface 131. The central hollow portion of the deflector interface 302 and/or the central hollow portion of the end effector assembly body 301 may be configured to receive and allow the longitudinal movement of wires, for example, at least actuator wire 160. The actuator wire 160 may be connected to the grasper jaws 303, for example, so that longitudinal movement of the actuator wire 160 with respect to the end effector assembly body 301 and/or the deflector interface 302 may cause the grasper jaws 303 to open and close. In another example, the end effector assembly 300 and the distal portion 130 may be one continuous piece of material.

Any end effector assembly, including any suitable end effectors and arrangement for actuating the end effectors, may be used with deflecting mechanisms according to this invention. As shown in the exemplary embodiment depicted in FIG. 5, end effector assembly 300 includes a bar linkage 304 connected at a proximal end to the distal end of actuator wire 160 and at a distal end to portions of grasper jaws 303. Bar linkage 304 may include, corresponding to each grasper jaw, a proximal link connected to a distal link. The proximal ends of the grasper jaws 303 connect to the distal ends of the proximal links, and the proximal ends of the proximal links connect together, pivot about each other, and connect to the actuator wire 160. Distal movement of the actuator wire 160 may cause the links to move and the grasper jaws 303 to open (i.e. the distal ends of the grasper jaws 303 to move away from each other). Proximal movement of the actuator wire 160 may cause the bar linkages 304 to move and the grasper jaws 303 to close (i.e. the distal ends of the grasper jaws 303 to move towards each other).

The end effector assembly 300 and/or grasper jaws 303 may also be used to apply a coagulation current and/or cauterize tissue. Currents may be run to the grasper jaws 303 by actuator wire 160 or other wires. The contact areas between the grasper jaws 303 (e.g., the pivot surface), or other end effectors, may be insulated from one another, by a washer, insulative layer or other spacer constructed of a non-conductive material such as TFE (Teflon), both to prevent short-circuiting and so that current is only applied when the opposing grasper jaws 303 are either in contact with each other or are simultaneously grasping an object (e.g., tissue). The application of the current to the tissue via the grasper jaw may have therapeutic effects on the tissue such as cauterizing the tissue.

FIG. 5 depicts an exemplary embodiment of handle portion 400 of the device 1. Handle portion 400 is generally configured to be easily grasped and/or handled by the user. Handle portion 400 may have an interface 403 on distal end 401. Interface 403 may be configured to connect with handle interface 203 of elongate member 200. Interface 403 may be hollow and communicate with the central hollow portion of the elongate member 200. Interface 403 may expand from having a small cross-sectional area at its distal end to a larger cross-sectional area at its proximal end. At its proximal end, interface 403 connects to central shaft 404 of handle portion 400. Central shaft 404 may have a substantially constant cross-sectional area along its entire length and may be made of a material that facilitates sliding of, for example, actuation handle 405 and deflection handle 409 along its length. Actuation handle 405 and deflection handle 409 may be in the form of a spool, or may be in any other suitable configuration to move actuator wire 160 and deflector wire 150, respectively. Central shaft 404 may be one continuous piece or multiple pieces, for example, a central shaft actuation portion 412 and a central shaft deflection portion 413, joined by the central stop 408 and/or multiple central stops.

As shown in the exemplary embodiment of FIG. 5, central shaft 404 has various parts of handle 400 disposed around it. The various parts may be coaxial with the central shaft 404. For example, an actuation handle is disposed near distal end 401 of handle portion 400. Actuation handle 405 may be coaxial with and disposed around central shaft 404, or at least central shaft actuation portion 412 of central shaft 404. Actuation handle 405 is slidable along central shaft actuation portion 412 of central shaft 404, for example, between the distal end of central stop 408 and the proximal end of connector interface 403.

Inside of actuation handle 405 is actuator wire interface portion 407 which connects actuator wire 160 to actuation handle 405. Any suitable method of attaching actuator wire 160 to actuation handle 405 is acceptable, for example, adhesives or set screws. For example, one or more set screws may extend through actuator wire interface portion 407 on actuation handle 405 to lock actuator wire 160 in place with respect to actuation handle 405. Actuation handle 405 also includes a recessed actuation grasping portion 406 disposed between the proximal and distal ends of actuation handle 405 to allow the user to better grasp and move actuation handle 405 with respect to central shaft 404. Actuator wire interface portion 407 may also include an active cord connector that connects the actuator wire 160 to an electrical current, for example, a cautery current from a remote current generator. In cases where there are two actuator wires 160, there may be two actuator wire interface portions 407 each having an active cord connector, or actuator wire interface portion 407 may have two active cord connectors each connected to one of the actuator wires 160.

A deflection handle 409 is disposed near the central and/or proximal portion of handle 400. Deflection handle 409 may be coaxial with and disposed around central shaft 404, or at least central shaft deflection portion 413 of central shaft 404. Deflection handle 409 slides along central shaft deflection portion 413 of central shaft 404, for example, between the proximal end of central stop 408 and the distal end of proximal stop 414 on proximal end 402. Inside of deflection handle 409 is a deflector wire interface portion 411 which connects deflector wire 150 to deflection handle 409. Any suitable method of attaching the deflector wire 150 to the deflection handle 409 is acceptable, for example, adhesives or set screws. For example, a set screw may extend through deflector wire interface portion 411 on deflection handle 409 to lock deflector wire 150 in place with respect to deflection handle 409. Deflection handle 409 also has a recessed deflection grasping portion 410 disposed between the proximal and distal ends of deflection handle 409 to allow the user to better grasp and move deflection handle 409 with respect to central shaft 404.

The proximal end 402 of handle portion 400 includes proximal stop 414. Proximal stop 414 may be disposed around central shaft 404 or may be configured to receive and connect with central shaft 404. Both central stop 408 and proximal stop 414 may be easy to grasp. For example, their size, weight, composition, and/or texture may vary depending on various handling requirements. In an example, handle portion 400 may be made of molded plastic. Central stop 408 and proximal stop 414 may be configured to be fixed relative to central shaft 404, however, they may also be movable, for example, to adjust the length of central shaft deflection portion 413 and/or central shaft actuation portion 412. Adjusting the length of central shaft portions 412, 413 will limit or extend the movement of actuation handle 405 and deflection handle 409, respectively, proximally and/or distally along central shaft 404, thereby altering the amount of actuation of the end effectors (degree of opening of grasper jaws, for example) and deflection of the deflecting mechanism.

Deflector wire 150 connects to a portion of handle portion 400 and extends through central shaft 404 of handle portion 400 and into body 201 of elongate member 200. More specifically, deflector wire 150 connects to the deflector wire interface portion 411 of the deflection handle 409. Deflector wire 150 enters proximal end 121 of proximal portion 110 of deflecting mechanism 10, through proximal opening 118. Once through proximal opening 118, deflector wire 150 extends within wire shaft 116 between wire gap wall 117, sidewalls 123, and wire containing wall 115. Moving distally in proximal portion 110, defector wire 150 extends past the distal end of wire containing wall 115 into distal gap 119 between pivot interfaces 112, 132 and between ends 173 of pivot couplings 171. As depicted in FIG. 5, a portion of deflector wire 150 at least in the vicinity of pivot portion 170 may be located slightly towards the wire gaps 114, 134.

Deflector wire 150 extends into proximal end 143 of distal portion 130 of deflecting mechanism 10 between sidewalls 144 and wire gap 134 and into wire shaft 136. Upon reaching distal end 142 of distal portion 130, deflector wire 150 connects to deflector wire connector 141 located at distal end 142 of wire gap wall 137, as set forth above.

Actuator wire 160 may be disposed within and with respect to deflecting mechanism 10 and other components of the device 1 in a manner similar to deflector wire 150 as set forth above. Generally, actuator wire 160 extends substantially parallel to deflector wire 150 for the vast majority of their lengths, and thus may be positioned and configured similarly to deflector wire 150 as set forth above. Some differences in position and connection exist, which will be described. For example, the position of connection of actuator wire 160 to handle portion 400 may differ. Actuator wire 160 connects to actuator wire interface portion 407 of actuation handle 405. The actuator wire interface portion 407 connects actuator wire 160 to actuation handle 405 by screws, adhesives, or any other suitable method known in the art. Actuator wire 160 then extends distally through a central hollow portion of central shaft 404 and into interfaces 403, 203. From there, actuator wire 160 extends through elongate member 200 and into the proximal end of deflector interface 202. Once actuator wire 160 is in distal end 142 of distal portion 130 and in wire shaft 136, it exits distal portion 130 (and hence deflecting mechanism 10) through distal opening 138.

Actuator wire 160 then connects to end effector assembly 300. Actuator wire 160 enters and extends through interface 302 of end effector assembly 300, into the proximal end of end effector assembly body 301, and through at least a portion of body 301 until it connects to end effector assembly 300. In the embodiment, actuator wire 160 connects to a proximal end of bar linkages 304, as shown in FIG. 5. Longitudinal movement of actuator wire 160 with respect to handle portion 400, elongate member 200, deflecting mechanism 10, and end effector assembly 300 causes grasper jaws 303 to open and close.

Wires 150 and 160 may be comprised of any suitable flexible material and may be any suitable cross-sectional size for fitting within an endoscopic medical device. In addition, actuator wires 150 and 160 may have different sizes and/or be made of different materials. For example, actuator wire 160 may be insulated along its entire length by a jacket of suitable material such as TFE (Teflon), and may be configured to conduct electricity. Actuator wire 160 may also be two wires, and each wire may be configured to conduct a current, while also being insulated to prevent short-circuiting. One end of the actuator wire 160 or wires may be connected to an actuator wire interface portion 407 which may include an active cord connector configured to deliver electricity from a power source to the actuator wire 160 or wires, for example, a cautery current from a remote power generator. The other end of the actuator wire 160 may be connected to end effector assembly 300. For two wires 160, each wire may be connected to an opposing jaw of grasper jaws 303 that are insulated from each other. When the opposing jaws are closed around an object (e.g., tissue) and/or brought into contact with each other, an applied current may flow through them, for example, to coagulate tissue.

Deflecting mechanism 10 also may be made of any suitable biocompatible material, such as metal, plastic, rubber, or other synthetic or natural materials. In other embodiments of deflecting mechanism 10, proximal portion 110 and distal portion 130 may have non-circular cross-sections, such as oval or hexagonal, deflecting mechanism 10 may have more than two portions, and/or more than one wire for deflecting the distal end in multiple directions. For example, one wire may be responsible for deflecting the distal end in one direction, and the other wire may be responsible for deflecting the distal end in another direction, for example an opposite direction.

To deflect the distal end of device 1, a user manipulates handle 400 to cause movement of the deflector wire 150. The user moves the deflection handle 409 relative to the central shaft 404. The user may first grasp either the central stop 408 or the proximal stop 414 with one hand, and then with the other hand grasp the deflection handle 409, for example, at the deflection grasping portion 410. The user then may move the deflection handle 409 proximally along the central shaft 404 of the central shaft deflection portion 413. Movement of deflection handle 409 away from central stop 408 and towards proximal stop 414 pulls wire 150 in handle 400, increasing the length of the deflector wire 150 in the handle 400. For example, the deflection handle 409 may move the deflector wire 150 proximally with respect to the rest of the handle portion 400, such that a portion of the deflector wire 150 previously in and around the handle interface 203 of the elongate member 200 may exit the handle interface 203 and enter the handle portion 400 through interface 403. In some embodiments, the distal end of the proximal stop 414 may come into contact with the proximal end of the deflection handle 409 and prevent further proximal movement of the deflection handle 409 along the central shaft 404. Accordingly, further intake of the deflector wire 150 into the central shaft 404 of the handle portion 400 may be prevented.

This movement of handle 409 and wire 150 causes the deflector wire 150 in elongate member 200 to shift longitudinally relative to the elongate member 200. This causes at least a portion of the deflector wire 150 in the proximal portion 110 of the deflecting mechanism 10 to move towards the proximal end 121 of the proximal portion 110, and some of the deflector wire 150 that was previously in the distal portion 130 of the deflecting mechanism 10 to enter the wire shaft 116 of the proximal portion 110 through the distal gap 119 and/or the wire gap 114. The length of the deflector wire 150 actually within the confines of the proximal portion 110 may stay the same length, but may also be shorter due to this movement of the deflector wire 150. For example, the deflector wire 150 may originally have extended from the distal gap 119 on the distal end 122 of the proximal portion 110, through the wire shaft 116, and finally through the proximal opening 118 of the proximal end 121 of the proximal portion 110. However, due to the movement of the deflector wire 150, while the deflector wire 150 may still run through the proximal opening 118 of the proximal end 121 of the proximal portion 110, on the opposite end of the proximal portion 110, the deflector wire 150 may now run through a portion of the wire gap 114 as opposed to the distal gap 119. Further movement of the deflector wire 150 may cause the deflector wire 150 to move in the distal gap 114 closer to the wire gap wall 117. This may be due to the interaction between the proximal portion 110, the distal portion 130, and the pivot portion 170. Details of this interaction are set forth below.

In the distal portion 130 of deflecting mechanism 10, the movement of the deflector wire 150 may cause the deflector wire 150 to try to move towards and through the proximal gap 139 of the distal portion 130 and the distal gap 119 of the proximal portion 110. However, because wire 150 connects to the distal portion 130 at the deflector wire connector 141, wire 150 is prevented from moving through the proximal gap 139. Accordingly, the deflector wire 150 may come under tension between a force from the handle portion 400 attempting to pull the deflector wire 150, and the deflector wire connector 141 on the distal portion 130 of the deflecting mechanism 10. Tension on the deflector wire 150 causes the distal portion 130 of the deflecting mechanism 10 to pivot at its pivot interface 132, so that wire gaps 114, 134 rotate towards each other, the external surfaces of the wire containing walls 115, 135 rotate away from each other, and the external surfaces of the wire gap walls 117, 137 rotate towards each other. The distal end 142 of the distal portion 130 likewise pivots around its pivot interface 132 towards the side of the distal portion 130 containing the wire gap 134 and wire gap wall 137. Rotation of the distal portion 130 with respect to the proximal portion 110 around the pivot interfaces 112, 132 of the pivot portion 170 continues until the user ceases the movement of the deflector wire 150. Rotation of the distal portion 130 with respect to the proximal portion 110 also may stop when some portion of the distal portion 130, for example the wire gap wall 137 or sidewalls 144, either enters the wire shaft 116 through the wire gap 114 or comes into contact with a distal part of the wire gap wall 117 on the proximal portion 110.

During the movement and/or rotation of the proximal portion 110 and distal portion 130 of the deflecting mechanism 10 with respect to each other, the position of the deflector wire 150 gradually changes. Initially, the deflector wire 150 runs from the handle portion through the elongate member 200, the proximal portion 110, and the distal portion 130 such that the deflector wire 150 is contained within and substantially parallel to the longitudinal axes of the above components. During the movement and/or rotation of the proximal portion 110 and distal portion 130 of the deflecting mechanism 10, however, the deflector wire 150 exits the confines proximal portion 110 and distal portion 130 through the wire gaps 114, 134. Accordingly, as depicted in the exemplary embodiment shown in FIG. 1a, the deflector wire 150 moves closer to the distal end of the wire gap wall 117 and exits the proximal portion 110 through a portion of the wire gap 114. Depending on the amount the distal portion 130 of the deflecting mechanism 10 has pivoted, the deflector wire 150 exits the proximal portion 110 closer to the distal side 122 or the wire gap wall side 117 of the wire gap 114. If the distal portion 130 of the deflecting mechanism 10 pivots such that a portion of its sidewalls 144 or wire gap wall 137 enter the wire gap and contact the distal end of the wire gap wall 117 of the proximal portion 110, the deflector wire 150 enters the distal portion 130 through the wire gap 134 while it is still also in the wire shaft 116 of the proximal portion 110.

Controlling the movement of the deflector wire 150 controls how much the distal portion 130 pivots with respect to the proximal portion 110 of the deflecting mechanism 10. Once the user decides the distal portion 130 has rotated enough and the desired angle has been achieved, the user ceases manipulating the handle portion 400 by stopping the movement of the deflection handle 409 relative to the rest of the handle portion 400 of the device 1. This stops the movement of the deflector wire 150 and ceases the rotation of the distal portion 130 around the pivot portion 170. Device 1 may include a means to lock the deflection handle 409 with respect to the rest of the handle portion 400 so that the deflecting mechanism retains its position without a user needing to hold deflection handle 409 in place.

Once the rotation of the distal portion 130 of the deflecting mechanism 10 has stopped, the user can manipulate the actuator wire 160 of the device 1. Accordingly, the user grabs the handle portion 400 of the device 1 and moves the actuation handle 405 relative to the central shaft 404. Specifically, the user first grabs either the central stop 408 or the proximal stop 414 with one hand, and then with the other hand grabs the actuation handle 405 at the actuation grasping portion 406. The user then moves the actuation handle 405 distally along the central shaft 404 of the central shaft actuation portion 412, away from the distal end of the central stop 408, and towards the interface 403. The movement of the actuation handle 405 shortens the length of the actuator wire 160 in the handle portion 400, and moves the actuator wire 160 distally with respect to the rest of the handle portion 400 and the elongate member 200. In some embodiments, there may be a mechanism for preventing the distal movement of the actuation portion past a certain point with respect to the central shaft 404 and/or the rest of the handle portion 400.

Upon user manipulation of the handle portion, the actuator wire 160 moves with respect to the elongate member 200 and the deflecting mechanism 10. Specifically, the actuator wire 160 moves with respect to the elongate member 200 and the deflecting mechanism 10 in a manner substantially similar to the deflector wire 150 as set forth above, except that the actuator wire 160 moves distally instead of proximally. The movement of the actuator wire 160 distally causes end effector assembly 300 of the device 1 to actuate, for example, the grasper jaws 303 to open. Moving the actuator wire 160 distally causes the joints of the opposing bar linkages 304 to spread and hence cause the grasper jaws 303 to open (i.e. the distal ends of the grasper jaws 303 to spread apart) due to the common distal joint for the opposing linkages 304.

The user continues to manipulate the handle portion 400 until either the user decides the end effector assembly 300 has been adequately actuated, or the handle portion 400 physically stops the actuation. There are various reasons why and how the user decides that the end effector assembly 300 of the device 1 has been adequately actuated, for example, whether the grasper jaws 303 have been sufficiently opened. For example, the user may have a view of the grasper jaws 303 through a visual component of an endoscope, and may decide that the grasper jaws 303 has been sufficiently opened so that they are in an ideal position to grab, for example, a lesion. In another example, the user may decide that the grasper jaws 303 should be opened a specific distance. In such an example, there may be predetermined markings or specific mechanisms (for example, locks or additional adjustable stops) on the handle portion 400 that allow a user to ascertain exactly how much movement of the actuation handle 405 of the handle portion 400 will allow the grasper jaws 303 to open the desired distance.

Once the grasper jaws 303 are open, the grasper jaws 303 are advanced further into the tissue tract or bodily organ, for example, to grasp a lesion. In order to grasp a lesion, the user manipulates the handle portion 400 of the device 1 to cause the actuator wire 160 to move proximally. Specifically, the user grabs or continues to hold either the central stop 408 or the proximal stop 414 with one hand, and with the other hand grabs or continues to grab the actuation handle 405 at the actuation grasping portion 406. Once the user has grabbed or continued to grasp the actuation grasping portion 406, the user moves the actuation handle 405 proximally along the central shaft 404 of the central shaft actuation portion 412, and towards the distal end of the central stop 408 and away from the connector interface 403. The movement of the actuation handle 405 lengthens the length of the actuator wire 160 in the handle portion 400, and moves the actuator wire 160 proximally with respect to the rest of the handle portion 400 and the elongate member 200. In some embodiments, the distal end of the central stop 408 may prevent the proximal movement of the actuation portion past a certain point with respect to the central shaft 404 and/or the rest of the handle portion 400.

Upon user manipulation of the handle portion 400, the actuator wire 160 shifts proximally with respect to the elongate member 200 and the deflecting mechanism 10. Specifically, the actuator wire 160 moves with respect to the elongate member 200 and the deflecting mechanism 10 in a manner substantially similar to the proximal movement of the deflector wire 150 as set forth above. The proximal movement of the actuator wire 160 causes the grasper jaws 303 to close around the lesion and securely grasp the lesion. More specifically, the grasper jaws 303 have a cross-bar linkage 304 that, upon moving the actuator wire 160 proximally, causes the joints of the opposing bar linkages 304 to come together and hence cause the grasper jaws 303 to close (i.e. the distal ends of the grasper jaws 303 to come together).

At this point, if desired for a particular procedure, the user may manipulate the handle portion 400 of the device 1 to cause the deflector wire 150 to move distally with respect to the elongate member 200 and causes the deflecting mechanism 10 to return to its original, substantially straight configuration. To do this, the user grabs or continues to grab the deflection handle 409 at the deflection grasping portion 410 and either the central stop 408 or the proximal stop 414. The user then moves the deflection handle 409 proximally along the central shaft 404, towards the distal end of the central stop 408, and away from the distal end of the proximal stop 414. The movement causes the deflector wire 150 to shift proximally in the central hollow portion of the central shaft 404, and reduce the length of the deflector wire 150 in the central shaft 404. The deflector wire 150 then shifts proximally in the entire length of the elongate member 200. The proximal shift of the deflector wire 150 causes the portion of the deflector wire 150 in the deflecting mechanism 10 to lengthen, and hence causes the deflecting mechanism 10 to straighten out. Specifically, the portion of the deflector wire 150 that exited the deflecting mechanism 10 through the wire gaps 114, 134 now reenters the deflecting mechanism 10 through those same wire gaps 114, 134 and is now once again completely contained within the deflecting mechanism 10. The lengthening of the deflector wire 150 pushes the distal portion 130 at the deflector wire connector 141. The pushing causes the external portions of the wire containing walls 115, 135 to rotate towards each other and the external portions of the wire gaps walls 117, 137 to rotate away from each other. Once the deflecting mechanism 10 has straightened, returned to its original configuration and/or assumed any other desired angle, the deflection handle 409 ceases moving proximally either due to user manipulation, its abutment against the proximal end 408, or some other structural mechanism in the handle portion 400.

In an exemplary embodiment, the device 1, and its various components may have various dimensions. For example, the length of the elongate member 200 connecting the handle portion 400 to the deflecting mechanism 10 may be about 72 cm. In another example, the length of the deflecting mechanism 10, when the proximal portion 110 and the distal portion 130 are engaged, may be about 11 mm. Of that, the length of the proximal portion 110 may be about 7 mm. The length of the end effector assembly 300, for example, including grasper jaws 303 may be about 19 mm. It should be understood, however, that these dimensions are only exemplary, and that the device 1 and its various components may have any dimensions necessary or desired.

In various methods of using device 1 with deflecting mechanism 10, device 1 may be placed in the desired tissue tract or internal organ in combination with and/or through the use of an endoscope. The endoscope may be placed at the desired tissue tract location using any suitable method known in the art. The device 1 may be advanced into the tissue tract through a working channel or lumen of the endoscope. Once the device 1 exits the distal end of the endoscope and is positioned at the desired location in the tissue tract, the user deflects the deflecting mechanism 10 and actuates the end effector assembly 300 as set forth above. Once the user has completed manipulating the deflecting mechanism 10 and/or the end effector assembly 300, the user may retract the device 1 out of the working channel or lumen of the endoscope. Any suitable, known methods of visualizing the site and/or procedure may be used, including various electronic imaging techniques.

In various methods of using the device 1 with deflecting mechanism 10, it may be desirable to apply current to an object, for example, apply a monopolar or bipolar coagulation current to tissue to cauterize the tissue. In such a method, the tissue may be grasped using the grasper jaws 303 or any other end effector assembly 300, as set forth above. For a monopolar current, the end effector assembly 300 may be connected to a current that, when brought into contact with the tissue, delivers the current to the tissue. For a bipolar current, each opposing jaw of the grasper jaws 303 may be connected to an opposing current that, when opposing jaws 303 are either brought together or grasp tissue, completes the connection and delivers the current to the tissue. This delivery of current to the tissue may have various therapeutic effects, for example, cauterizing the tissue.

In various other exemplary methods, device 1 with deflecting mechanism 10 may be used in conjunction with a full thickness resection device (FTRD), for example, of the type disclosed in U.S. Pat. No. 6,398,795 to McAlister et al. The FTRD may be used in combination with an endoscope as described in that patent. In this exemplary embodiment, the FTRD extends over the endoscope and accommodates the device 1. As an initial step in the method, the user uses a method known in the art to advance an endoscope into the body and gain access to the treatment site via the endoscope. The user then advances the FTRD along the endoscope until the FTRD is positioned at the treatment site.

Once the FTRD is positioned at the treatment site, an opening is formed at the distal end of the FTRD. The opening may be on any portion of the distal end of the FTRD and may face in any direction from the FTRD. As an example, the opening is formed on the side of the distal end and faces a direction perpendicular to the longitudinal axis of the FTRD. The device 1 with the deflecting mechanism 10 and grasper jaws 303 is then advanced to the treatment site through the FTRD. The advancement may occur at any time, for example, prior, during, or after positioning the FTRD at the treatment site and/or prior, during, or after forming the opening in the FTRD. Once the device 1 is positioned at the treatment site, the user deflects the deflection mechanism 10 as set forth above. At this point, portions of the device 1, for example the end effector assembly 300 and/or a part of the distal portion 130 of the deflecting mechanism 10, may extend through the distal opening on the FTRD and out into the tissue tract or other bodily organ. In the alternative, however, the grasper jaws 303 of the device 1 may be advanced through the opening on the FTRD and out into the tissue tract or other bodily organ after deflection of the deflecting mechanism 10.

Once the grasper jaws 303 have advanced through the FTRD distal opening, the user positions the grasper jaws 303 next to the lesion and grabs the lesion with the grasper jaws 303 as set forth above. The user then brings the lesion into the FTRD by straightening the deflecting mechanism 303 and/or retracting device 1 into the FTRD. Once the grasper jaws 303 and the lesion are fully through the opening of the FTRD, the user actuates a portion of the FTRD that cuts the lesion off of the tissue tract or bodily organ. Substantially simultaneously with, or shortly after, the cutting of the lesion, the FTRD staples the portions of the tissue tract or bodily organ formerly around the lesion together so as to close the cut portion. Stapling the tissue portions may prevent infection and/or facilitate healing of the tissue tract and/or bodily organ. Once the desired tissue section has been cut and the surrounding tissue has been stapled, the user removes the cut tissue from the body. This may be done by retracting the device 1 and/or the FTRD out of the body.

In the various embodiments, device with a deflecting mechanism according to the invention may be used in any suitable medical procedure, including any endoscopic procedure, and in any suitable non-medical procedure. In the various embodiments, the end effector assembly may be any type of medical or non-medical end effector, for example other grasping devices, biopsy jaws, snares, baskets, suction devices, cutters, screwdrivers, aspiration devices, and fluid delivery devices, among other things. The device 1 may also be used in various non-medical procedures.

In the various embodiments, a device with a deflecting mechanism according to the invention may have various alternative configurations. For example, the user's manipulation of the handle may include turning a knob, pushing a button, pulling a handle, or it may even be an oral command to an electronic mechanism. The connection of the end effectors (such as graspers) to the actuation mechanism may also have various configurations known in the medical device or other mechanical arts.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. An end effector apparatus comprising:
    a flexible insertion section, a distal portion of which is configured for insertion to a target site within a living body;

a handle at a proximal end of the insertion section which remains outside the body when the distal portion of the insertion section is inserted into the body to the target site;

a deflecting mechanism at a distal end of the insertion section, the deflecting mechanism having a proximal member and a distal member pivotally coupled to one another and open to one another via a proximal end gap in the proximal end of the distal member and a distal end gap in the distal end of the proximal member, the proximal and distal members including proximal and distal side gaps, respectively, the proximal side gap extending to the distal end of the proximal member laterally of the distal end gap and the distal side gap extending to the proximal end of the distal member laterally of the proximal end gap to form a continuous opening with the proximal side gap;

an end effector assembly coupled to the distal end of the deflecting mechanism;

a first actuator member extending from the handle through the insertion section to couple to the distal member so that actuation of the first actuator member pivots the distal member relative to the proximal member between a longitudinally aligned configuration and a deflected configuration; and a second actuator member extending from the handle through the insertion section to the end effector assembly to actuate the end effector assembly a proximal opening and a side gap defined by the deflecting mechanism, wherein each of the first and second actuator members extends between the proximal and distal members via the distal and proximal end gaps when the proximal and distal members are in the longitudinally aligned configuration and extend therebetween via the proximal and distal side gaps when the proximal and distal members are in the deflected configuration.

2. The apparatus of claim 1, wherein the first actuator member is a wire.

3. The apparatus of claim 2, wherein the wire extends through a lumen defined by the deflecting mechanism.

4. The apparatus of claim 3, wherein the wire is coupled to the deflecting mechanism to allow the wire to move within the lumen.

5. The apparatus of claim 1, wherein the second actuator member is a wire.

6. The apparatus of claim 5, wherein the wire extends through a lumen defined by the deflecting mechanism.

7. The apparatus of claim 6, wherein the wire is coupled to the deflecting mechanism to allow the wire to move within the lumen.

8. The apparatus of claim 5, wherein the end effector assembly includes links, the end effector being connected to the links.

9. The apparatus of claim 1, wherein the distal member pivots relative to the proximal member about at least one pin extending through holes defined by the proximal and distal portions.

10. The apparatus of claim 1, wherein the end effector assembly includes a grasper.

11. The apparatus of claim 1, wherein the end effector assembly includes a medical device.

12. The apparatus of claim 1, wherein the deflecting mechanism is configured to allow the distal member to pivot up to at least 90 degrees relative to an axis of the proximal portion.

13. The apparatus of claim 1, wherein the deflecting mechanism is configured to allow the distal member to deflect in only one direction relative to the proximal portion.

14. The apparatus of claim 1, wherein the end effector assembly is configured to receive a current.

15. The apparatus of claim 1, wherein the proximal and distal side gaps are defined by a side portion of the deflecting mechanism.

16. The apparatus of claim 1, wherein a pivot joins the distal end of the proximal member and the proximal end of the distal member.

17. An end effector apparatus comprising:
a flexible insertion section, a distal portion of which is configured for insertion to a target site within a living body;

a handle at a proximal end of the insertion section which remains outside of the body when the distal portion of the insertion section is inserted into the body to the target site;

a deflecting mechanism at a distal end of the insertion section, the deflecting mechanism having a proximal member and a distal member pivotally coupled to one another and open to one another via a proximal end gap in the proximal end of the distal member and a distal end gap in the distal end of the proximal member, the proximal and distal members including proximal and distal side gaps, respectively, the proximal side gap extending to the distal end of the proximal member laterally of the distal end gap and the distal side gap extending to the proximal end of the distal member laterally of the proximal end gap to form a continuous opening with the proximal side gap;

an end effector assembly coupled to the distal end of the deflecting mechanism; and a first actuator member extending from the handle through the insertion section to couple to the distal member so that actuation of the first actuator member pivots the distal member relative to the proximal member between a longitudinally aligned configuration and a deflected configuration, wherein the first actuator member extends between the proximal and the distal members via the distal and proximal end gaps when the proximal and distal members are in the longitudinally aligned configuration and extend therebetween via the proximal and distal side gaps when the proximal and distal members are in the deflected configuration.

18. The apparatus of claim 17, further comprising a second actuator member extending from the handle through the insertion section to the end effector assembly to actuate the end effector assembly.

19. The apparatus of claim 18, wherein the second actuator member extends between the proximal and distal members via the distal and proximal end gaps when the proximal and distal member are in the longitudinally aligned configuration and extends therebetween via the proximal and distal side gaps when the proximal and distal members are in the deflected configuration, 20. The apparatus of claim 17, wherein the proximal and distal side gaps are defined by a side portion of the deflecting mechanism.

21. The apparatus of claim 17, wherein a pivot joins the distal end of the proximal member and the proximal end of the distal member.

22. An end effector apparatus comprising:
- a flexible insertion section, a distal portion of which is configured for insertion to a target site within a living body;
- a deflecting mechanism at a distal end of the insertion section, the deflecting mechanism bending between a longitudinal configuration in which the deflecting mechanism is substantially straight and a deflected configuration in which the deflecting mechanism is bent to form an arc, the deflecting mechanism including a lateral opening extending longitudinally along a portion of a wall thereof;
- an end effector assembly coupled to the distal end of the deflecting mechanism;
- a first actuator member extending through the insertion section to couple to a distal portion of the deflecting mechanism so that actuation of the first actuator member bending the deflecting member from the longitudinal configuration to the deflected configuration; and
- a second actuator member extending through the insertion section to the end effector assembly to actuate the end effector assembly wherein, when the deflecting mechanism is in the deflected configuration, the first and second actuator members extend across the arc outside the deflecting mechanism via the lateral opening and, when the deflecting mechanism is in the aligned configuration, the first and second actuator members are fully received therewithin.

* * * * *